US006725078B2

(12) United States Patent
Bucholz et al.

(10) Patent No.: US 6,725,078 B2
(45) Date of Patent: Apr. 20, 2004

(54) SYSTEM COMBINING PROTON BEAM IRRADIATION AND MAGNETIC RESONANCE IMAGING

(75) Inventors: Richard D. Bucholz, St. Louis, MO (US); D. Douglas Miller, St. Louis, MO (US)

(73) Assignee: St. Louis University, St. Louis, MO (US)

(*) Notice: Subject to any disclaimer, the term of this patent is extended or adjusted under 35 U.S.C. 154(b) by 444 days.

(21) Appl. No.: 09/754,852

(22) Filed: Jan. 4, 2001

(65) Prior Publication Data

US 2001/0049475 A1 Dec. 6, 2001

Related U.S. Application Data

(60) Provisional application No. 60/179,271, filed on Jan. 31, 2000.

(51) Int. Cl.[7] .............................................. A61B 5/05
(52) U.S. Cl. ...................................... 600/410; 600/407
(58) Field of Search ................................ 600/410, 411, 600/407; 324/307, 308, 309

(56) References Cited

U.S. PATENT DOCUMENTS

| 3,428,307 | A | | 2/1969 | Hunter et al. |
| 4,019,059 | A | | 4/1977 | Brundin et al. |
| 4,233,662 | A | * | 11/1980 | LeMay ........................ 600/425 |
| 4,481,657 | A | | 11/1984 | Larsson |
| 4,589,126 | A | | 5/1986 | Augustsson et al. |
| 4,771,785 | A | | 9/1988 | Duer |
| 5,039,867 | A | | 8/1991 | Nishihara et al. |
| 5,117,829 | A | | 6/1992 | Miller et al. |
| 5,327,884 | A | | 7/1994 | Hardy et al. |
| 5,412,823 | A | | 5/1995 | Sitta |
| 5,443,068 | A | | 8/1995 | Cline et al. |
| 5,511,549 | A | * | 4/1996 | Legg et al. .................. 600/436 |
| 5,547,454 | A | * | 8/1996 | Horn et al. ..................... 600/1 |
| 5,647,361 | A | | 7/1997 | Damadian |
| 5,790,996 | A | | 8/1998 | Narfström |
| 5,993,373 | A | * | 11/1999 | Nonaka et al. ................. 600/1 |
| 6,094,760 | A | * | 8/2000 | Nonaka et al. ................. 5/601 |
| 6,207,952 | B1 | * | 3/2001 | Kan et al. ................. 250/252.1 |

FOREIGN PATENT DOCUMENTS

| DE | 3828639 A1 | 3/1989 |
| WO | WO99/27839 A1 | 6/1999 |

* cited by examiner

*Primary Examiner*—Thomas Denion
*Assistant Examiner*—Daniel Robinson
(74) *Attorney, Agent, or Firm*—Senniger, Powers, Leavitt & Roedel

(57) ABSTRACT

A system which coordinates proton beam irradiation with an open magnetic resonance imaging (MRI) unit to achieve near-simultaneous, noninvasive localization and radiotherapy of various cell lines in various anatomic locations. A reference image of the target aids in determining a treatment plan and repositioning the patient within the MRI unit for later treatments. The patient is located within the MRI unit so that the target and the proton beam are coincident. MRI monitors the location of the target. Target irradiation occurs when the target and the proton beam are coincident as indicated by the MRI monitoring. The patient rotates relative to the radiation source. The target again undergoes monitoring and selective irradiation. The rotation and selective irradiation during MRI monitoring repeats according to the treatment plan.

17 Claims, 6 Drawing Sheets

SYSTEM COMBINING PROTON BEAM IRRADIATION AND MAGNETIC RESONANCE IMAGING

BACKGROUND OF THE INVENTION

1. Field of the Invention

The present invention relates to systems for localization and radiotherapy of various cell lines in various anatomic locations. In particular, this invention relates to a system which coordinates proton beam irradiation with an open magnetic resonance imaging (MRI) unit to achieve near-simultaneous, noninvasive localization and radiotherapy of various cell lines in various anatomic locations by maintaining coincidence between the target and the proton beam.

2. Description of the Prior Art

Proton beam irradiation therapy treats tumors found in selected locations that are not subject to significant physiologic motion. Examples of such tumors include prostatic cancer, spinal chordomas, and certain retinal or orbital tumors. The proton beam generated by a medical cyclotron has similar biological activity for the destruction of tumors as standard radiation therapy techniques to target a fixed tumor site with minimal radiotoxicity to the surrounding normal tissues. Because protons of a specific energy have a specific penetration depth, adjusting the specific energy of the protons manipulates the distance the proton beam travels into the patient. Because protons deposit most of their energy at the end of the penetration depth, the highest concentration of radiation occurs in the area around the penetration depth. This area is known as the Bragg peak of the proton beam.

The focused delivery of protons to a fixed site permits the radiotherapy of tumors or the destruction of tissue causing functional problems. However, tumors and tissue located in organs subject to significant physiologic motion cannot be treated without significant collateral radiotoxicity. There is a need for a system which allows proton beam delivery to a target subject to significant physiologic motion that minimizes the collateral damage to the surrounding normal tissues.

SUMMARY OF THE INVENTION

It is an object of this invention to provide a system which treats a target within a body of a patient by proton beam therapy by using a scanner to locate the target.

It is another object of this invention to provide a system which coordinates a treatment volume such as a Bragg peak of a proton beam with a target detected noninvasively such as a tumor or dysfunctional tissue to be destroyed as detected by MRI.

It is another object of this invention to provide such a system which includes a patient support device to position the patient so that the target is located within the treatment volume.

It is another object of this invention to provide such a system which includes a patient support device that allows irradiation of the target at multiple angles while maintaining coincidence between the target and the treatment volume.

It is another object of this invention to provide a system which treats a target within a body of a patient by proton beam therapy by allowing irradiation of the target at multiple angles according to a treatment plan while minimizing radiation of surrounding tissues during the physiologic motion of the target.

It is another object of this invention to provide a method for irradiating at multiple angles a target subject to significant physiologic motion within a body of patient.

In one form, the invention comprises a system for treating a target within a body of a patient comprising a radiating apparatus, a patient support, a scanner, and a controller. The radiating apparatus irradiates a treatment volume having a known position. The patient support supports the patient such that the target to be treated is located coincident with or adjacent to the treatment volume. The scanner scans the body and creates body images. The controller selectively activates the radiating apparatus to irradiate the target when the target is at least partially coincident with the treatment volume.

In another form, the invention includes a method for treating with a radiating apparatus a target within a patient resting on a patient support rotatable about a rotational axis, the method comprising the steps of:

positioning the patient support such that the target is at least partially coincident with or adjacent to a treatment volume irradiated by the radiating apparatus and the target and treatment volume lie along the rotational axis;

selectively irradiating the treatment volume when the target is at least partially coincident with the treatment volume;

rotating the patient relative to the radiating apparatus; and again selectively irradiating the treatment volume while monitoring the location of the target in the adjusted position.

In one form, the method of the invention treats a target within a body of a patient with a radiating apparatus irradiating a treatment volume having a known position by the following steps:

positioning the patient such that the target to be treated is located near the treatment volume;

scanning the body and creating body images of the body to determine the position of the target relative to the treatment volume; and activating the radiating apparatus to irradiate the target when the determined position of the target is at least partially coincident with the known position of the treatment volume.

In another form, the invention comprises a system for treating a target within a body of a patient, wherein the system comprises:

a radiating apparatus irradiating a treatment volume having a known position;

a scanner scanning the body and creating body images of the body to determine the position of the target; and a controller responsive to the scanner for activating the radiating apparatus to irradiate the target when the position of the target as determined by the scanner is at least partially coincident with the known position of the treatment volume.

Other objects and features will be in part apparent and in part pointed out hereinafter.

Those skilled in the art will note that the drawings are not to scale and certain shapes and volumes have been enlarged for viewing convenience.

DETAILED DESCRIPTION OF PREFERRED EMBODIMENTS

In general, the system 100 of the invention is a near-simultaneous, noninvasive localization and radiotherapy device capable of detecting and treating malignancies, benign tumors, and normal tissues of various cell lines in any anatomic location within the body.

Magnetic resonance imaging (MRI) is a noninvasive diagnostic imaging technique which uses powerful magnetic fields and rapidly changing radio-frequency energy pulses to tomographically represent the varied fat and water content within living tissues. Using standard, cylindrical, closed-bore magnet designs, MRI is extremely useful for the detection and localization of tumors, some of which may not be detected using X-ray computed tomography (CT). The open-architecture design of newer MRI units (e.g., units 156) has extended the utility of standard MRI by permitting the imaging of claustrophobic patients, and by permitting intra-operative imaging in real time during surgery. Proton beam therapy can be combined with MRI or other scanners to minimize collateral radiotoxicity to the surrounding normal tissues by gating the delivery of the proton beam (e.g. beam 111) during physiologic cycles.

The primary physiologic cycles considered are the respiratory and cardiac cycles. However, other physiological movements, such as those related to voluntary or involuntary muscular activity (such as peristalsis), can also be accommodated with this technique. Because abdominal as well as diaphragmatic movement may adjust the position of the tumor during the respiratory cycle, the position of the patient must be adjusted for each of these movements. Rapid MRI acquisition minimizes the need for patient breath-holding during treatment.

While open MRI units are required in the preferred embodiment of the present invention, it is acknowledged that other embodiments of the present invention may be compatible with standard, closed-bore MRI units. It is not intended that such embodiments be outside the scope of the present invention, and, in fact, any type of compatible MRI may be used.

Further, while it is acknowledged that MRI systems are currently the only scanners compatible with the other technologies required in the present invention, it is not intended that the present invention be limited to such scanning systems, and, in fact, any compatible scanner capable of imaging the body may be used.

Figure 1:
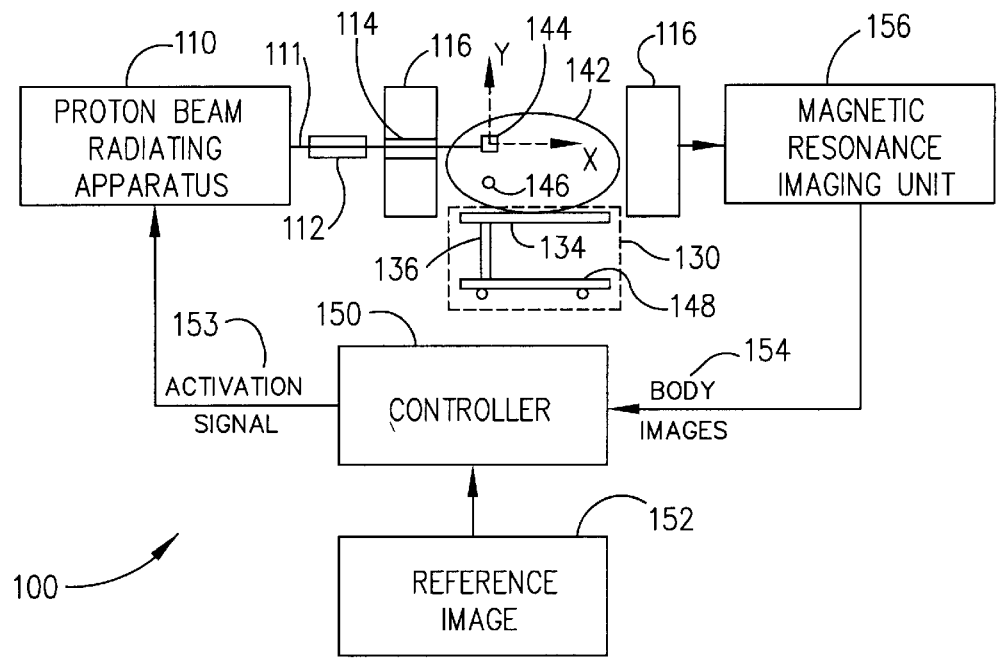
FIG. 1 is a block diagram of one preferred embodiment of the system according to the invention in which a controller selectively activates a proton beam radiating apparatus, including a partial end elevation view of a patient support.

Referring first to FIG. 1, a block diagram illustrates the main components of one preferred embodiment of a system of the present invention. A patient 142 has tumorous tissue, such as a target 146, to be irradiated by a proton beam 111. A proton beam radiating apparatus 110 located outside of a pair of magnets 116 of an MRI unit 156 emits the proton beam 111 which first passes through an optional water attenuator 112. The proton beam 111 then passes through an optional beam pipe 114 located within one of the magnets 116 before entering the patient 142. The proton beam 111 focuses on a treatment volume 144 within the patient 142 and is activated when the treatment volume 144 is at least partially coincident with the target 146. The attenuator 112 and beam pipe 114 are used, if needed, to position the treatment volume 144 between the magnets 116. Activation of the proton beam radiating apparatus 110 occurs through the use of an activation signal 153 received from a controller 150. The controller 150 sends the activation signal 153 when body images 154 received from the MRI unit 156 indicate that the target 146 as defined by a reference image 152 from an earlier MRI scan overlaps the treatment volume 144. The reference images 152 reside in memory accessible by the controller 150.

Figure 4:
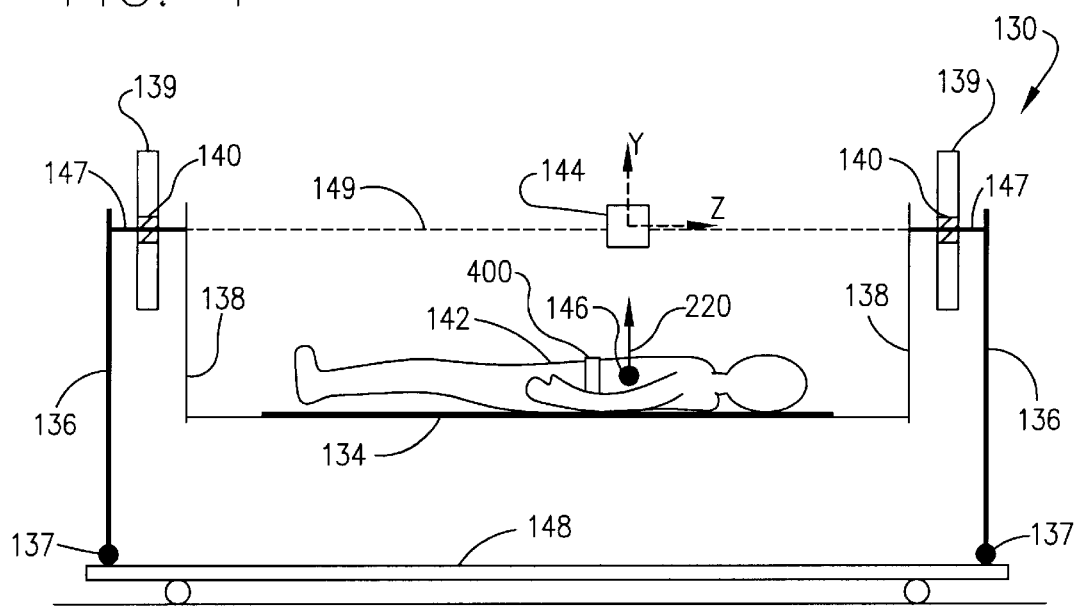
FIG. 4 is a lateral elevation view of the patient support showing the patient on the platform of the patient support.

The patient 142 rests on a patient support 130 comprising a substantially horizontal platform 134 supported by a pair of upright supporting mechanisms 136 on either end of the platform 134 (e.g., head and toe) connected to a base frame 148 on casters. The patient support 130 resides between the magnets 116 of the MRI unit 156. The patient support 130 adjusts within an XYZ-axis coordinate system. The X-axis extends side to side along the width of the patient 142. The Y-axis extends front to back along the depth of the patient 142, substantially perpendicular to the base frame 148. The Z-axis, as shown in FIG. 4, extends from head to toe along the longitudinal axis defining the height of the patient 142. The operation of the system of FIG. 1 will be described below.

Figure 2:
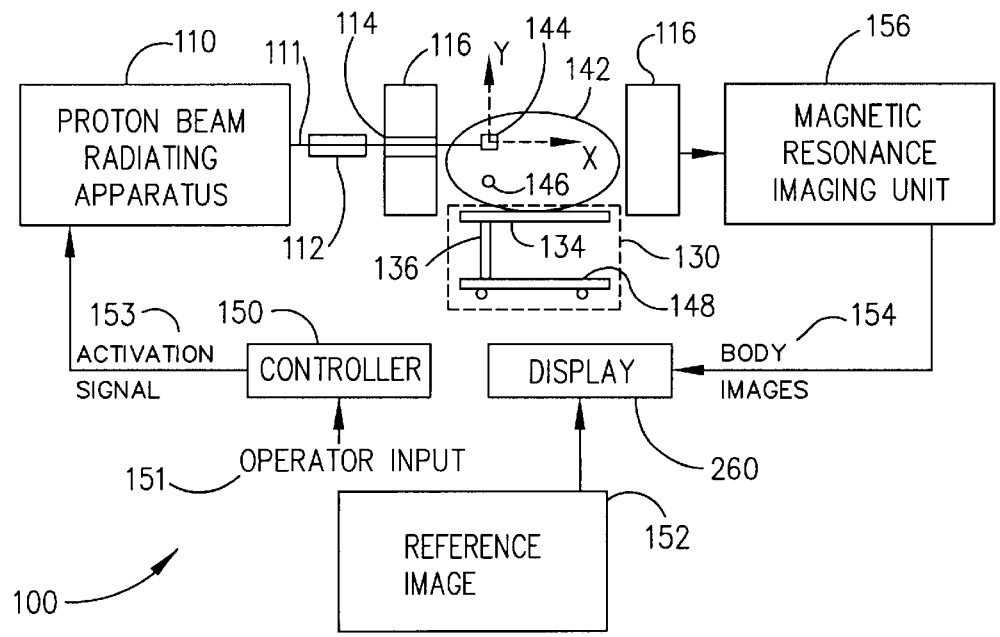
FIG. 2 is a block diagram of another preferred embodiment of the system according to the invention in which the controller selectively activates the proton beam radiating apparatus in response to operator input from an operator viewing a display of body images and a reference image.

Referring next to FIG. 2, the components and their connections correspond to FIG. 1 except that the body images 154 and the reference image 152 appear on a display 260 viewed by an operator 151 who manually controls the system rather than providing the images to the controller 150 for automatically controlling the system. While viewing the display 260, the operator 151 signals the controller 150 via a keyboard or touch-screen to provide operator input to send the activation signal 153 to the proton beam radiating apparatus 110 to activate the proton beam 111 selectively. The operator 151 signals the controller 150 to send the activation signal 153 when the body images 154 received from the MRI unit 156 indicate that the target 146 at least partially overlaps the treatment volume 144. Similarly, the operator 151 signals the controller 150 to send the de-activation signal when the body images 154 indicate that the target 146 has moved out of coincidence with the treatment volume 144. The operation of the system of FIG. 2 will be described below.

Figure 3:
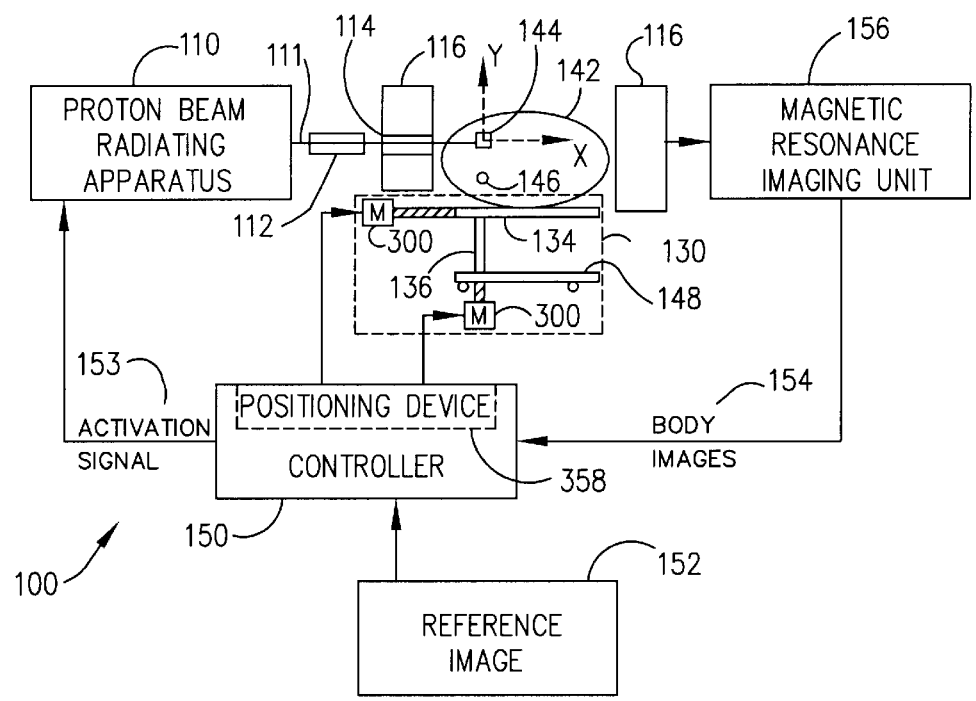
FIG. 3 is a block diagram of another preferred embodiment of the system according to the invention in which the patient support is adjusted during irradiation to maximize the time the treatment volume and target are coincident or adjacent.

Referring next to FIG. 3, the components and their connections correspond to FIG. 1 with the addition of motors 300 connected to the patient support 130. The motors 300 operate in response to a positioning device 358 (e.g., a control board) within the controller 150 to adjust the patient support 130 to maximize the time that the target 146 and treatment volume 144 are coincident. The motors 300 may be energized to move the target 146 so that it at least partially overlaps the treatment volume 144. Alternatively, the motors 300 may be energized to counter physiologic motion to maintain the target 146 within the treatment volume 144. For example, because breathing represents a common physiologic cycle, in one embodiment the motors 300 could raise or lower the platform 134 to offset any down or up breathing motion of the patient 142 which maximizes the time that the target 146 and treatment volume 144 are coincident. The operation of the system of FIG. 3 will be described below.

The potential repositioning action during the treatment to achieve maximal time of coincidence with the treatment volume 144 may create mechanical and radio-frequency (RF) noise which could effect the MRI quality. Repositioning the platform 134 in the Z-axis only to account for the majority of respiratory variability should maximize treatment time in the target window while minimizing noise.

Referring next to FIG. 4, a lateral elevation view of the patient support 130 is shown. Initially, the patient 142 is placed on the platform 134 and moved into position along the Z-axis so that the target 146 and the treatment volume 144 are located in or near the same vertical X-Y plane. As FIG. 4 indicates, the target 146 and treatment volume 144 may not be coincident and may be located in different, non-adjacent planes. The upright supporting mechanisms 136 connect to opposing ends of the base frame 148 of the patient support 130 by gearings 137.

A pivot pin 147 protrudes from each upright supporting mechanism 136 to the interior of the patient support 130 along a Z-axis. The pivot pins 147 define a substantially horizontal, rotational axis 149 of the patient support 130 parallel to the Z-axis. A vertical patient rotation plate 139 with bearings 140 in its bored-out center is mounted on each pivot pin 147 to permit rotation of the plates 139 about the rotational axis 149 parallel to the Z-axis. A pair of vertical struts 138 attach to the pivot pins 147. One end of each strut 138 attaches to the ends of the pivot pins 147 interior to the patient support 130. The struts 138 engage and suspend the platform 134 containing the patient 142. One strut 138 attaches to the pivot pin 147 above the head of the patient 142 while the other strut 138 attaches to the pivot pin 147 below the foot of the patient 142. Movement of the platform 134 relative to struts 138 along the X-axis and/or movement of the upright support mechanism 136 relative to base frame 148 along the X-axis positions the patient 142 so that the target 146 and the treatment volume 144 are located in the same Y-Z plane.

Figure 5:
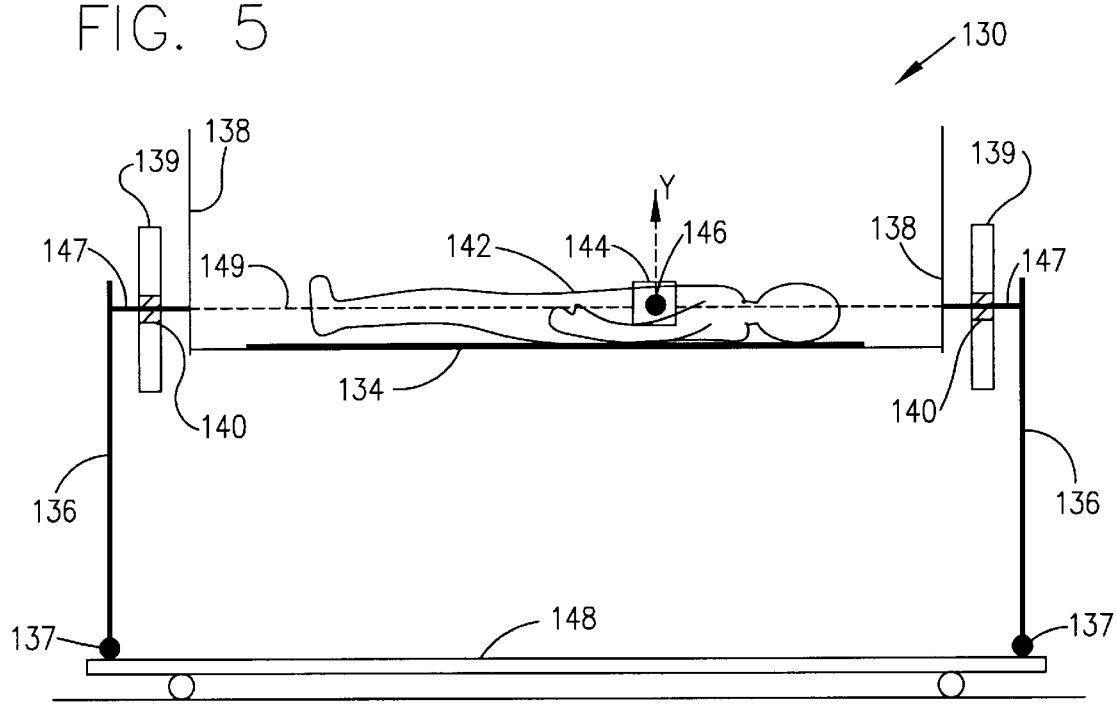
FIG. 5 is a lateral elevation view of the patient support showing the patient on the platform after the patient support has been adjusted so that the target and the rotational axis lie within the same substantially horizontal plane (e.g., X-Z plane).

Referring next to FIG. 5, the components and their connections correspond to FIG. 4 except that the portion of the struts 138 relative to pins 147 has been adjusted so that the target 146 and the treatment volume 144 are located in or near the same X-Z plane. The struts 138 have been repositioned as compared to FIG. 4 to raise the platform 134 along the Y-axis relative to the pivot pins 147 so that the target 146 and treatment volume 144 lie within the same substantially horizontal plane as the rotational axis 149.

Figure 6:
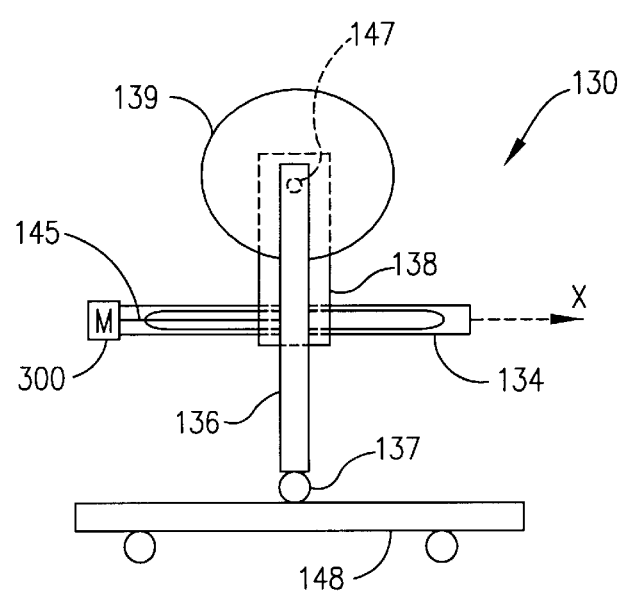
FIG. 6 is an end elevation view of the patient support wherein the upright supporting mechanism is centered on the base frame.
Figure 7:
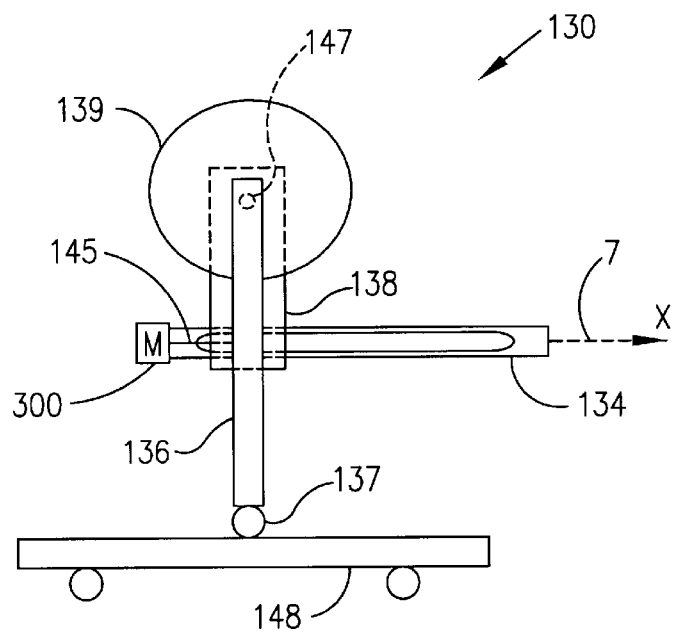
FIG. 7 is an end elevation view of the patient support wherein the platform has moved horizontally and is positioned to the right as compared to FIG. 6.

Referring next to FIG. 6, an end elevation view of the patient support 130 illustrates one preferred embodiment of the present invention in which the upright supporting mechanisms 136 is attached by the gearings 137 to the center of the end rails of the base frame 148. FIG. 6 shows the initial positions (similar to FIG. 4) of the elements of the patient support 130 relative to one another. The position of the platform 134 is adjustable along the X-axis by the motor 300 driving a mechanically threaded platform screw 145. The patient rotation plates 139 pivotally attach to the top ends of the upright supporting mechanisms 136. As the motor 300 which is affixed to platform 134 turns platform screw 145 which threadably engages the strut 138, the strut 138 moves closer to or away from the motor 300. As a result, platform 134 moves side to side relative to the strut 138, as shown in FIG. 7. In another embodiment, the gearings 137 are absent and the upright supporting mechanisms 136 are fixedly centered on the ends of the base frame 148. As above, the platform 134 moves side to side relative to the strut 138.

Referring next to FIG. 7, an end elevation view of the patient support 130 illustrates one preferred embodiment of the present invention in which the upright supporting mechanisms 136 is mounted on the gearings 137 moveable along the X-axis and platform 134 is moveable along the X-axis relative to the struts 138. It is contemplated that either the gearings 137 and/or the platform screw 145 may permit movement of the platform 134 along the X-axis. FIG. 7 shows the position of the platform 134 after it has been moved to the right relative to the struts 138 by the motor 300, the platform 134 moving in the direction as indicated by an arrow 7.

Figure 8:
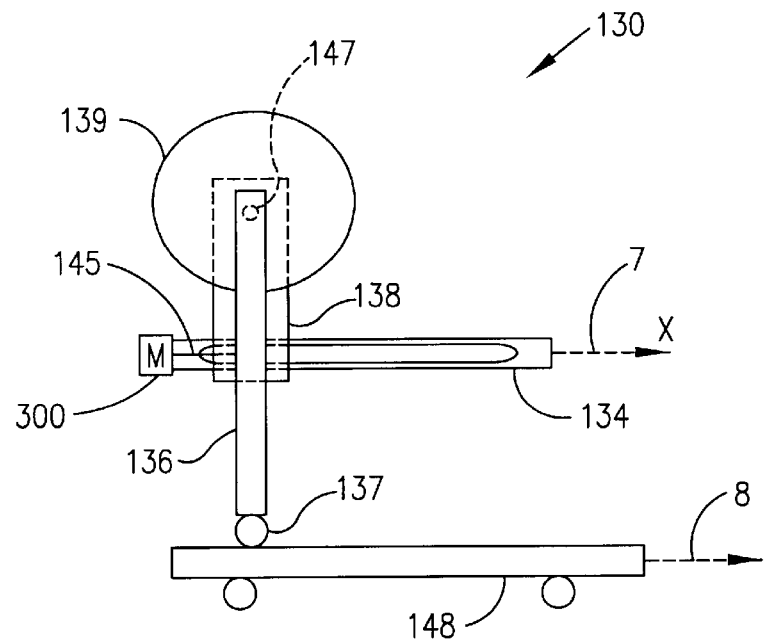
FIG. 8 is an end elevation view of the patient support wherein the upright supporting mechanism has moved horizontally to the left so that the platform (positioned to the right) is centered over the base frame.

Referring next to FIG. 8, the components and their connections correspond to FIG. 7 except that the base frame 148 has been moved via the gearings 137 along the X-axis as indicated by an arrow 8 to the right to center the platform 134 over the base frame 148.

Figure 9:
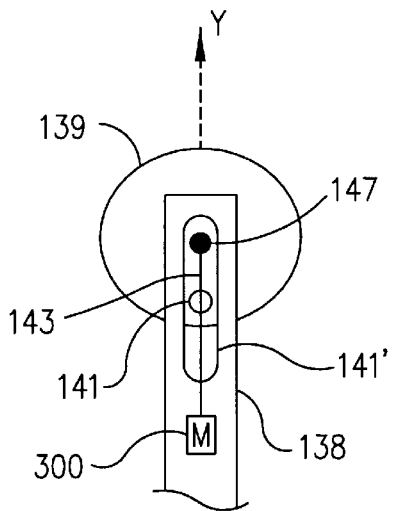
FIG. 9 is a partial end elevation view of the patient support illustrating the operation of the strut screw drive as it moves the strut along the patient rotation plate in a substantially vertical fashion.

Referring next to FIG. 9, a partial end elevation view (from the interior toward the exterior) illustrates one of the patient rotation plates 139 and its connection to the strut 138. The pivot pin 147 protrudes along the Z-axis from the upright supporting mechanism 136 (not shown in FIG. 9), through the patient rotation plate 139 to the strut 138. The strut 138 adjusts along the Y-axis by the motor 300 connected to a mechanically threaded strut screw drive 143. A guide pin 141 located near the perimeter of the patient rotation plate 139 extends from the patient rotation plate 139 through the strut 138 into a slot 141 to cause the patient rotation plate 139 and strut 138 to rotate together about the Z-axis.

Figure 10:
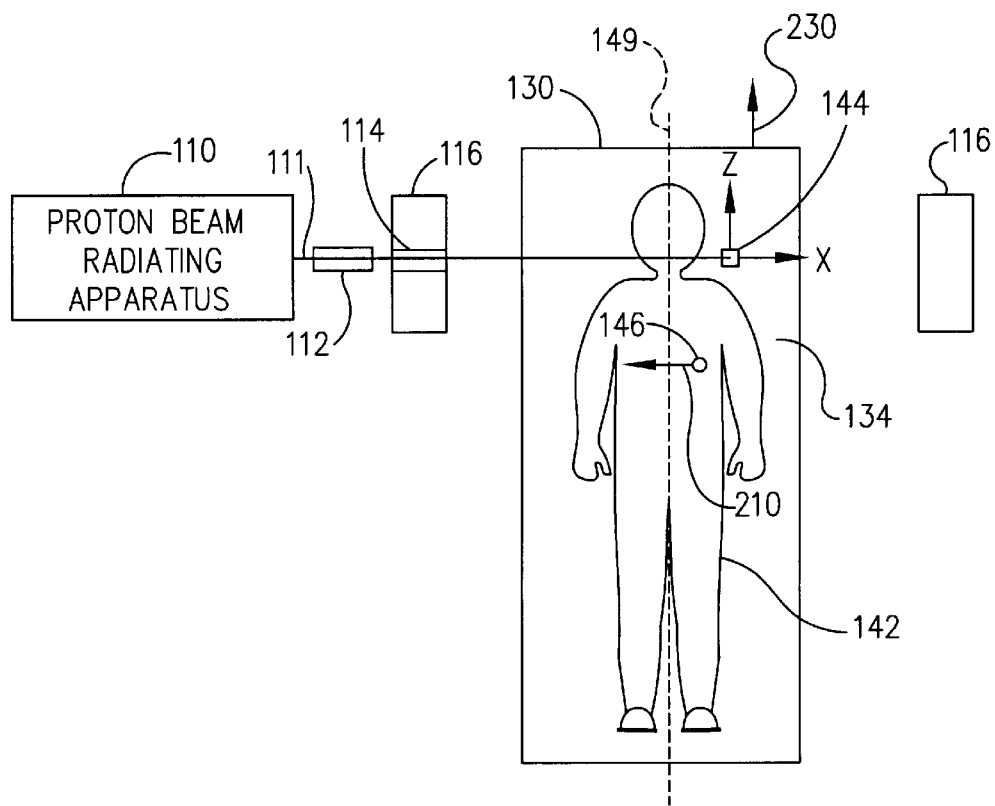
FIG. 10 is a partial top elevation view of the patient on the patient support before adjustment of the patient support.

Referring next to FIG. 10, a top view of the patient 142 on the patient support 130 within the magnets 116 illustrates that the target 146 and treatment volume 144 are initially not coincident. The patient 142 rests on the patient support 130 located between the two magnets 116 of the MRI unit 156. The proton beam 111 enters the MRI unit 156 through the beam pipe 114 and focuses on the treatment volume 144.

Figure 11:
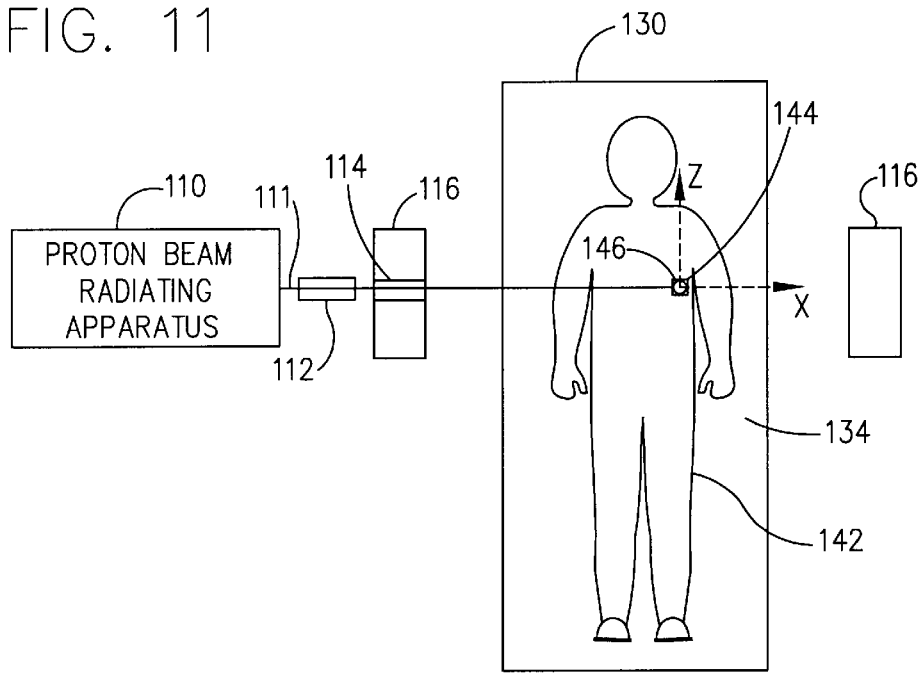
FIG. 11 is a partial top elevation view of the patient on the patient support after-the patient support has been adjusted within the MRI magnets so that the target and treatment volume lie within the same substantially horizontal plane.

Referring next to FIG. 11, the components and their connections correspond to FIG. 10 except that the position of platform 134 and patient 142 has been adjusted so that the target 146 and treatment volume 144 are coincident. The patient support 130 has been moved along the X and Z axes (as noted above) to achieve coincidence in the X-Y and X-Z planes between the target 146 and treatment volume 144. Alternatively, the proton beam 111 may be attenuated so that the target 146 and treatment volume 144 align along the X-axis. The platform 134 may also be moved along the Y-axis (as noted above) to achieve coincidence in the X-Z plane.

In general, the invention comprises the system 100 for treating the target 146 within the body of the patient 142, wherein the system comprises:

the radiating apparatus 110 irradiating the treatment volume 144 having the known position;

the scanner 116, 156 scanning the body 142 and creating the body images 154 of the body to determine the position of the target 146; and the controller 150 responsive to the scanner 116, 156 for activating the radiating apparatus 110 to irradiate the target 146 when the position of the target 146 as determined by the scanner 116, 156 is at least partially coincident with the known position of the treatment volume 144.

Operation

To irradiate the target 146 within the patient 142, the treatment plan evolves as follows. The MRI unit 156 pre-operatively scans the patient 142 to obtain the reference image 152 of the target 146. Based on this reference image 152 and its location within the patient 142, the treatment plan incorporates the number and angle of the irradiations. The reference image 152 also aids in relocating the target 146 after repositioning the patient 142 within the MRI unit 156 for subsequent treatments.

Paramagnetic agents are used for tumor enhancement. It is anticipated that paramagnetic agents may be utilized during treatment for patient positioning. These agents can have physiologic effects (e.g., gadolinium reduces the heart rate) which may require an adjustment of the proton beam gating.

It is contemplated that injectable agents can interact with the beam on a dose determined basis. These agents would vary their MRI characteristics during treatment so that the MRI scan would indicate when a specific amount of dose had reached the target, and also indicate any scatter of radiation within the patient, to assist in the delivery of radiation to the patient. In this way any error in the treatment plan could be compensated for during the actual treatment.

To implement the treatment plan, the target 146 within the patient 142 and the treatment volume 144 must be at least partially coincident. The treatment volume 144 is the location of the Bragg peak for the proton beam 111. The patient 142 is positioned on the support 130 and the support 130 is placed between the two magnets 116 of an open MRI unit 156 as illustrated in FIG. 1 and FIG. 4. The MRI unit 156 provides body images 154 of the patient 142 to the controller 150 or operator 151 searching for the area of the location of the reference image 152 within the patient 142. When the body images 154 correspond to the reference image 152 and locate the target 146, the position of the patient 142 on the patient support 130 is adjusted as noted above along the Y and Z axes so that the target 146 lies along the X-axis path of the proton beam 111. Attenuating the proton beam 111 with the water attenuator 112 adjusts the location of the treatment volume 144 along the X-axis so that the target 146 and the treatment volume 144 are at least partially coincident or adjacent. Alternatively, the position of the patient 142 on the patient support 130 may be adjusted as noted above along the X-axis so that the target 146 at least partially coincident with the treatment volumes 144 so that the attenuation of the proton beam 111 need not be changed.

The target 146 may shift as a result of physiologic motion (e.g., the respiratory or cardiac cycle). Because the target 146 may be subject to significant physiologic motion, the controller 150 or the operator 151 selectively activates the proton beam 111 when the target 146 and treatment volume 144 are at least partially coincident. In a preferred embodiment, the controller 150 automatically gates the proton beam 111 based on feedback circuits and body images 154 to maximize the amount of treatment that the target 146 receives while in the treatment volume 144. In the preferred embodiment, the controller 150 uses a physiologic trigger based on the respiratory cycle which has been previously evaluated by MRI to estimate the normal extent of diaphragmatic excursion. However, in general, the controller 150 need only control activation and deactivation of the proton beam 111 and, in one form, may be a timer to activate the beam for a set period.

Operator 151 control presumably would introduce inefficiency and delay in the operation of the proton beam 111 reducing the amount of time that treatment is delivered to the target 146. However, a respiratory device 400 around the patient 142 determines the onset of inspiration which acts as a signal for treatment to reduce operator 151 effort and controller 150 mistakes. Preferably, the respiratory device 400 is a stretchable belt that expands and contracts as the patient 142 inhales and exhales. Determining the onset of inspiration requires a pre-programmed abdominal and diaphragmatic motion range obtained from the pre-treatment MRI study.

When the target 146 moves out of the treatment volume 144, the controller 150 or the operator 151 signals the proton beam radiating apparatus 110 to de-activate the proton beam 111. When the target 146 moves back within the treatment volume 144, the controller 150 or the operator 151 signals the proton beam radiating apparatus 110 to re-activate the proton beam 111. In this manner, irradiation of the moving target 146 occurs with minimal radiotoxicity to the normal surrounding tissues.

In another embodiment, adjusting the patient support 130 during irradiation to compensate for the physiologic motion of the target 146 maximizes the time that the target 146 and treatment volume 144 are coincident. A positioning device 358 within the controller 150 operates the motors 300 to adjust the position of the platform 134 along the X and Y axes. Motors (not shown) may also be used to rotate plate 139 and/or adjust the position of platform 134 along the Z-axis. The controller 150 determines whether the patient support 130 requires adjustment to improve the degree of coincidence of the target 146 and treatment volume 144. The controller 150 also determines the direction and distance of the adjustment. Those skilled in the art will note that the controller 150 could be designed to adjust the patient support 130 in any spatial dimension as well as rotation about the rotational axis 149. For example, because breathing represents a common physiologic cycle, in one embodiment the motors 300 could raise or lower the platform 134 by moving the struts 138 up or down with respect to the patient rotation plates 139 to offset the down and up breathing motion of the patient 142 and to maximize the time that the target 146 and treatment volume 144 are coincident.

Preferably, the patient 142 should be repositioned along the Z-axis to coordinate physiologic motion to treatment volume 144. Repositioning the patient 142 in anything other than the Z-axis in a time frame that would allow for the connection of physiologic motion to treatment activation may be more difficult to achieve. Further, prior to treatment, the normal respiratory cycle range of diaphragmatic excursion for the patient 142 as well as the maximum range of deep breathing can be determined. The impact of this respiratory range (normal and maximal) on liver and lung positioning can be used to program the controller 150 to move the patient support 130 to maximize coincidence between the target 146 and treatment volume 146 during treatment.

Figure 12:
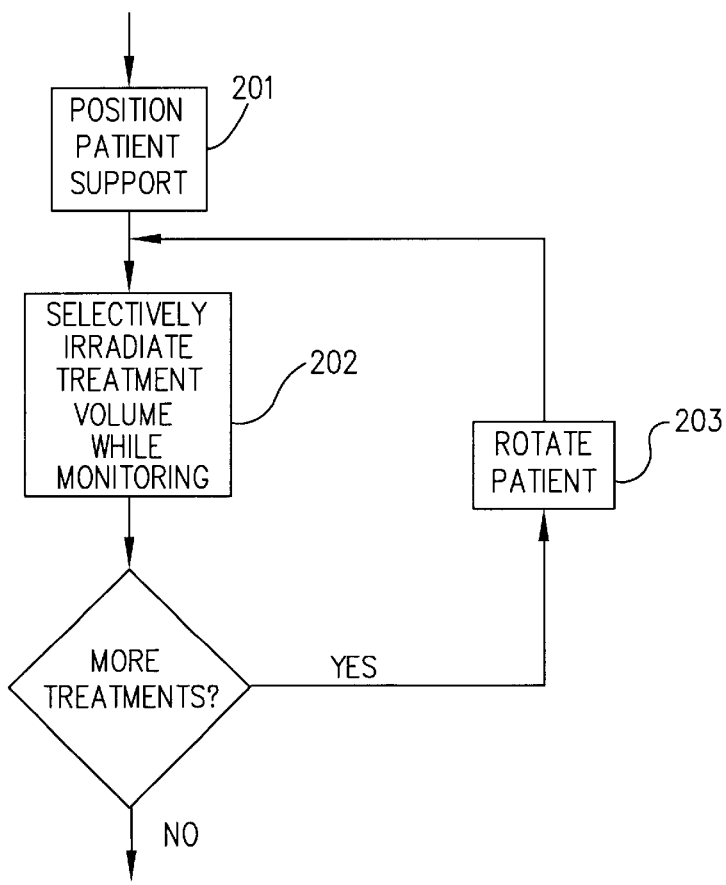
FIG. 12 is a flow chart illustrating the main steps of the treatment method used by the present invention.

Referring to FIG. 12, a flow chart illustrates the basic steps for irradiating the target 146. A first step 201 positions the patient support 130 appropriately. A second step 202 selectively irradiates the treatment volume 144 while monitoring the location of the target 146 with MRI. If successive irradiations are necessary, then a third step 203 rotates the patient 142 and performs additional monitored irradiations. The second and third steps 202, 203 repeat as many times as necessary after each rotation step 203 according to the treatment plan. The treatment ends when no more irradiations are required.

In particular, the first step 201 involves positioning the patient support 130 so that the target 146 within the patient 142 is coincident with or near the treatment volume 144 (i.e., Bragg peak) of the proton beam 111. The second step 202 irradiates the target 146 while the target 146 and the treatment volume 144 are at least partially coincident. The MRI monitors the location of the target 146 while the controller 150 or the operator 151 selectively activates and deactivates the proton beam radiating apparatus 110 as described above to minimize the collateral tissue damage. If successive irradiations are required from different angles according to the treatment plan, then in the third step the patient 142 is moved (e.g., rotated about the Y or Z axes) relative to the proton beam radiating apparatus 110 and again selectively irradiated. The patient 142 is rotated about the target 146 about the Y-axis by rotating the base frame 148 on its casters about the Y-axis. The patient 142 is rotated about the target 146 about the Z-axis by turning the patient rotation plates 139 about pin 147. Alternatively, the proton beam radiating apparatus 110 may rotate about the treatment volume 144. Proton accelerators are already manufactured which allow the beam pipe to rotate about the patient. This rotation could occur within the gap between the two magnet of the MRI unit. Preferably, the patient 142 rotates about the Z-axis relative to the proton beam radiating apparatus 110 approximately 80 degrees in either a clockwise or counterclockwise direction while maintaining the coincidence of the treatment volume 144 with the target 146. The rotation and selective irradiation of the target 146 repeats as many times as necessary according to the treatment plan.

The first step 201 in the method for irradiating the target 146, positioning the patient 142 so that the target 146 and treatment volume 144 are coincident, comprises several substeps which may be performed in various sequences. Those skilled in the art will recognize that there are several ways not specifically detailed herein to manipulate the patient support 130 to achieve coincidence between the target 146 and the treatment volume 144.

The first substep involves positioning the target 146 and the rotational Z-axis 149 within the same substantially vertical Y-Z plane by movement along the X-axis (see arrow 210 in FIG. 10). The position of the upright supporting mechanisms 136 adjust along the X-axis by a set of the gearings 137 as in FIG. 8. The platform 134 moves along the X-axis on the ends of the struts 138 by the mechanically threaded platform screw drive 145 as in FIG. 7. As the platform 134 is adjusted in one direction along the X-axis as in FIG. 7, the upright supporting mechanism 136 may be adjusted in the opposite direction as in FIG. 8 to maintain the position of the platform 134 centered over the base frame 148. The upright supporting mechanism 136 and platform 134 adjust in this manner until the target 146 and the rotational axis 149 lie within the same substantially vertical X-Y plane. Centering the platform 134 over the base frame 148 prevents the patient support 130 from tipping over due to the target 146 being located near either outer edge of the platform 134. If the upright supporting mechanisms 136 is fixedly attached to the base frame 148 (not shown), only the platform 134 moves along the X-axis to place the target 146 in the same vertical Y-Z plane as the rotational axis 149 or the base frame 148 moves on its casters to achieve the same result. In FIG. 10, the target 146 would be moved left.

The second substep in positioning the patient 142 involves adjusting the height of the platform 134 by movement along the Y-axis so that the target 146 and the rotational axis 149 lie within the same substantially horizontal X-Z plane (see arrow 220 in FIG. 4). Referring to FIG. 9, the mechanically threaded strut screw drives 143 attach to each strut 138. The strut screw drives 143 raise or lower the platform 134 along the Y-axis depending on the location of the target 146 so that the target 146 and the rotational axis 149 of the patient support 130 lie within the same substantially horizontal plane.

The third substep in positioning the patient 142 involves placing the target 146 within the path (or within the vertical X-Y plane) of the proton beam 111 by movement along the Z-axis. To locate the target 146 within the path of the proton beam 111, the patient support 130 is moved into place on its casters between the magnets 116 of the MRI (see arrow 230 in FIG. 10).

In the fourth substep to position the patient 142, the position of the target 146 is adjusted along the X-axis relative to the Bragg peak or treatment volume 144 of the proton beam 111 so that the treatment volume 144 is coincident with the target 146. In one embodiment, the location of the treatment volume 144 is adjusted along the X-axis by attenuating the proton beam 111 with the water attenuator 112. Those skilled in the art will notice that the attenuation of the proton beam 111 can be accomplished in several different ways not specifically described herein. Alternatively, the patient support 130 may be moved on its casters along the X-axis until the target 146 is near or coincident with the treatment volume 144.

An additional, fifth substep may be required to position the target 146 and the treatment volume 144 within the same substantially horizontal X-Z plane. Preferably, the vertical distance from the floor to the rotational axis 149 equals the distance from the floor to the center of the treatment volume 144. Since the target 146 has been aligned with the axis 149 by substeps one and two, this alignment is preset and this substep need not be performed. Alternatively, the upright supporting mechanism 136 may telescope along the Y-axis so achieve this alignment and perform this substep.

In general, the above substeps may be performed in various sequences. In one embodiment, the target is located in the XYZ grid using MRI and patient repositioning occurs through the use of skin surface markers relative to anatomic landmarks such as a thoracic spinal process or the xiphoid process. In another embodiment, the location of the target 146 is physically marked by marks on the patient 142 and each substep is performed by a technician who visually aligns the marks with the rotational axis 149 (substeps one and two) and aligns the marks with the treatment volume 144 (substeps three, four and five). Alternatively, each substep can be performed by using the MRI scans themselves which depict the target to locate the target 146 and comparing determined location with the known location of the treatment volume 144. As in FIGS. 1 and 2, the given reference image 152 has certain characteristics which allow the controller 150 or the operator 151 to recognize the target 146 as the MRI scan progresses. To identify the location of the target 146, the controller 150 or the operator 151 compares the body images 154 to the reference image 152. With knowledge of the path of the proton beam 111, the controller 150 or the operator 151 further adjusts the patient support 130 so that the target 146 lies within the path of the proton beam 111.

In one aspect, it is important that the target 146 be aligned with the rotational axis 149. With this alignment, rotation about the rotational axis 149 does not require any realignment or performing any of the substeps over again after rotation.

In general, the method of the invention treats the target 146 within the body of the patient 142 with the radiating apparatus irradiating the treatment volume 144 having the known position by the following steps:

positioning the patient 142 such that the target 146 to be treated is located near the treatment volume 144;

scanning the body and creating the body images 154 of the body to determine the position of the target 146 relative to the treatment volume 144; and activating the radiating apparatus 110 to irradiate the target 146 when the determined position of the target 146 is at least partially coincident with the known position of the treatment volume 144.

The accompanying mechanics of the proton beam 111 and positioning devices may have variable effects on the MRI RF pulses, or on other magnetic fields and gradients ($B_1$). For example, the movement of heavy metal devices will affect the overall $B_0$ field, and may create "eddying" effects that could distort images. Such effects may require shielding or other compensation to avoid distorted images. Alternatively, the positioning device could be fabricated partially or totally out of materials that do not interfere with, or cause distortion in, the MRI scans. In addition, if the proton beam treatment changes the tissues per se and their imaging characteristics acutely or changes the physiology of respiration, these changes may require revised repositioning adjustments.

While particular embodiments of the invention have been shown and described, it will be obvious to those skilled in the art that various changes and modifications may be made without departing from the present invention in its broader aspects. It is intended that all matter contained in the above description and shown in the accompanying drawings shall be interpreted as illustrative and not in a limiting sense.

What is claimed is:

1. A system for treating a target within a body of a patient, said system comprising:

a radiating apparatus irradiating a treatment volume having a known position;

a patient support supporting the patient such that the target to be treated is located adjacent to the treatment volume;

a scanner scanning the body and creating body images of the body to monitor the position of the target; and a controller responsive to the monitored position of the target for selectively activating the radiating apparatus to irradiate the target when the target is at least partially coincident with the treatment volume and selectively deactivating the radiating apparatus when the target is not at least partially coincident with the treatment volume.

2. The system of claim 1 wherein the controller selectively activates and deactivates the radiating apparatus in response to operator input.

3. The system of claim 1 wherein the radiating apparatus comprises a proton beam radiating apparatus irradiating with a proton beam the treatment volume.

4. The system of claim 3 wherein the known position of the treatment volume is the location of a Bragg peak for the proton beam.

5. The system of claim 3 wherein the scanner comprises a magnetic resonance imaging scanner.

6. The system of claim 5 wherein the scanner comprises a coil magnet and wherein the radiation is positioned to pass through the coil magnet so that the radiation is constrained by the coil magnet.

7. The system of claim 1 wherein the radiating apparatus includes a radiation source and an attenuator for adjusting the known position of the treatment volume relative to the radiation source.

8. The system of claim 7 wherein the attenuator is a water attenuator.

9. The system of claim 1 wherein the scanner comprises a magnetic resonance imaging scanner.

10. The system of claim 9 wherein the scanner comprises a coil magnet and wherein the radiation is positioned to pass through the coil magnet so that the radiation is constrained by the coil magnet.

11. The system of claim 1 further comprising a reference image indicative of the target to be treated and wherein the controller determines a position of the target by comparing the body images to the reference image, said controller activating the radiating apparatus to irradiate the target when the determined position of the target is at least partially coincident with or adjacent to the known position of the treatment volume.

12. The system of claim 1 wherein the controller includes a positioning device including a position control for moving the patient support and wherein the position control is responsive to the controller to move the patient support so that the time during which the treatment volume and target are at least partially coincident or adjacent is maximized.

13. The system of claim 1 further comprising a respiratory device for determining respiration onset in the patient and wherein the controller is responsive to the device for selectively activating the radiating apparatus in coordination with respiration onset as detected by the device.

14. The system of claim 1 wherein the patient support comprises:

a base frame supporting the patient support;

a pair of upright supporting mechanisms connected to the base frame;

a pair of patient rotation plates connected to the upright supporting mechanism, said patient rotation plates rotatable about a substantially horizontal rotational axis;

a pair of struts connected to the patient rotation plates, said struts adjustable relative to the patient rotation plates in a substantially vertical fashion; and a platform adapted to support the body of the patient, said platform connected to the struts to rotate about the rotational axis, wherein the platform is adjustably spaced from the rotational axis by the struts such that the target is coaxial with or adjacent to the rotational axis when the body of the patient is on the platform.

15. A system for treating a target within a body of a patient, said system comprising:

a proton beam radiating apparatus having a Bragg peak irradiating a treatment volume having a known position;

a scanner scanning the body and creating body images of the body to determine the position of the target; and a controller responsive to the scanner for activating the radiating apparatus to irradiate the target when the position of the target as determined by the scanner is at least partially coincident with the known position of the treatment volume and deactivating the radiating apparatus when the position of the target as determined by the scanner is not at least partially coincident with the known position of the treatment volume.

16. A system for treating a target within a body of a patient, said system comprising:

means for irradiating a treatment volume having a known position;

means for supporting the patient such that the target to be treated is located adjacent to the treatment volume;

means for scanning the body and creating body images of the body to monitor the position of the target; and means responsive to the monitored position of the target for selectively activating the radiating apparatus to irradiate the target when the target is at least partially coincident with the treatment volume and selectively deactivating the radiating apparatus when the target is not at least partially coincident with the treatment volume.

17. A system for treating a target within a body of a patient, said system comprising:

means for radiating having a Bragg peak irradiating a treatment volume having a known position;

means for scanning the body and creating body images of the body to determine the position of the target; and means, responsive to the means for scanning, for activating the radiating apparatus to irradiate the target when the position of the target, as determined by the means for scanning, is at least partially coincident with the known position of the treatment volume, and for deactivating the radiating apparatus when the position of the target as determined by the means for scanning is not at least coincident with the known position of the treatment volume.

* * * * *